United States Patent [19]  [11] 3,960,658
Avakian et al.  [45] June 1, 1976

[54] MULTI-MEDIA PETRI DISH

[75] Inventors: Souren Avakian, Westport, Conn.;
Harry Seneca, Fort Lee, N.J.

[73] Assignee: Centaur Chemical Co., Stamford, Conn.

[22] Filed: Sept. 23, 1974

[21] Appl. No.: 508,182

[52] U.S. Cl. ........................ 195/103.5 R; 195/127;
195/100; 195/102; 195/139
[51] Int. Cl.² ........................ C12K 1/04; C12K 1/10
[58] Field of Search ............... 195/103.5 R, 4, 127,
195/99, 100, 101, 102, 139

[56] References Cited
UNITED STATES PATENTS

| | | | |
|---|---|---|---|
| 3,055,808 | 9/1962 | Henderson | 195/139 |
| 3,632,478 | 1/1972 | Fink | 195/103.5 R |
| 3,784,448 | 1/1974 | Cekoric, Jr. et al. | 195/103.5 R |
| 3,830,703 | 8/1974 | Beckford | 195/103.5 R |
| 3,832,288 | 8/1974 | Rollender et al. | 195/103.5 R |
| 3,842,166 | 10/1974 | Bucalo | 195/127 |

*Primary Examiner*—David M. Naff
*Assistant Examiner*—C. A. Fan
*Attorney, Agent, or Firm*—Buckles and Bramblett

[57] ABSTRACT

A disposable article of manufacture is provided which comprises a Petri-type dish which is divided into separate compartments containing culture media adapted for the rapid identification of uropathogenic bacteria and colony count determination.

3 Claims, No Drawings

MULTI-MEDIA PETRI DISH

BACKGROUND OF THE INVENTION

In scientific medical practice the clinician must determine the anatomical location of an infection, the nature of the causative agent and the drug susceptibility/resistance pattern. The routine cultural methods require a few days to identify the pathogenic agent. Rapid identification of the pathogen is helpful in prescribing proper antimicrobial medication.

Microbes are rapidly changing or evolving either because of sudden or gradual increase in drug resistance or through episomal transmission of drug resistance (resistance transmission factor or resistance factor). The list of antimicrobial drugs is constantly increasing and the choice of which drug to use in treating infections is a difficult one.

Since the recent introduction of the Kirby-Bauer scale in antimicrobial therapy by the Food and Drug Administration, the physician is warned indirectly to make bacterial cultures and to determine the drug susceptibility-resistance pattern of pathogens. All package inserts of antimicrobial drugs contain the range of effectiveness of that drug in the treatment of various pathogenic bacteria.

Numerous rapid chemical and bacteriological methods of diagnosis of urinary tract infection have been devised. The most primitive procedure is Gram or methylene blue stain of urinary sediment. It is claimed that a colony count of more than 100,000 bacteria per ml. shows bacteria in the smear.

The principle in the nitrite (Griess) test is the reduction of nitrate to nitrite by bacteria in urine. The triphenyltetrazolium chloride test (Uroscreen) is based on reduction of triphenyltetrazolium by bacteria to formazan which is a red precipitate. In the catalase test, bacteria and blood cells liberate oxygen from hydrogen peroxide. In the PathoTec test, chemically treated strips of filter paper are dipped into cultures of bacteria to identify phenylalanine deaminase, lysine decarboxylase, urease, citrase, indole and acetyl methyl carbinol production by bacteria. The enterotube method is a modification of PathoTec in which 8 media in a tube are inoculated from a bacterial culture to determine dextrose/dulcitol fermentation, lysine decarboxylation, urease, citrase, indole and $H_2S$ production. In R/B differential system for identification of Enterobacteriaceae, bacterial culture is inoculated to tube 1 for lactose/dextrose fermentation, phenylalanine deaminization, lysine decarboxylation and $H_2S$ production; while tube 2 is used for motility, indole production and lysine decarboxylation. In the Urocult test, medium is coated inside the tube which is filled with urine and then decanted. Sturdy bacteria grow on this crude medium and the colony count is very inaccurate. Another test is based on the production of adenosine triphosphate but non-bacterial adenosine triphosphate must be first eliminated. In the Bacti Lab test urine is spread on blocks of media (blood agar, eosin methylene blue, MacConkey's agar, triple sugar iron agar and urea agar) for fast-crude identification and colony count. UniTect medium is a modification of the Bacti Lab test. In the Unibac System a plate containing eosin methylene blue, blood agar, mannitol salt agar and mycobiotic dextrose agar is inoculated; while Mueller-Hinton medium is used for drug susceptibility.

The foregoing described chemical and bacteriological methods of diagnosis of urinary tract infection are useful advances, but these methods are not entirely satisfactory as either being not sufficiently rapid or not providing accurate and reliable data.

Accordingly, it is an object of the present invention to provide a method for rapid and accurate identification of uropathogenic bacteria and colony count determination.

It is another object to provide an article of manufacture which is inexpensive and disposable, and which is adapted for rapid identification of uropathogens.

Other objects and advantages will become apparent from the following description and examples.

DESCRIPTION OF THE INVENTION

One or more objects of the present invention are accomplished by the provision of a diagnostic kit for the rapid identification of uropathogenic bacteria which comprises a Petri-type dish which is designed as a compartmentalized receptacle, and which contains culture media in separate compartments comprising (1) a medium for lactose and sucrose fermentation, (2) a medium for urea splitting, (3) a medium for citrate utilization, and (4) a medium for hydrogen sulfide and indole production, and phenylalanine deamination.

Preferably, the diagnostic kit is an inexpensive and disposable article of manufacture which consists of a plastic Petri-dish which is divided into four separate compartments containing the appropriate culture media recommended for rapid identification of uropathogens.

The following examples are further illustrative of the present invention. The components of the culture media are presented as being typical, and various modifications can be devised in view of the foregoing disclosure within the scope of the invention.

EXAMPLE 1

Preparation of Culture Media

The culture media are sterilized by autoclaving at 15 pounds pressure and a temperature of 121°C. for 15 minutes. The urea solution is not autoclaved, but is sterilized by filtration through Seitz. The culture media component quantities are designated in grams.

| Medium 1 | |
|---|---|
| peptone | 10.00 |
| saccharose | 5.0 |
| lactose | 5.0 |
| dipotassium phosphate | 2.0 |
| eosin | 0.4 |
| methylene blue | 0.065 |
| agar | 15.0 |
| distilled water | 1,000.0 |

| Medium 2 | |
|---|---|
| peptone | 30.00 |
| beef extract | 3.0 |
| peptonized iron | 0.2 |
| sodium thiosulfate | 0.025 |
| DL-phenylalanine | 2.0 |
| agar | 15.0 |
| distilled water | 1,000.0 |

| Medium 3 | |
|---|---|
| magnesium sulfate | 0.2 |
| ammonium dihydrogen phosphate | 1.0 |
| disodium phosphate | 1.0 |
| sodium citrate | 2.0 |
| sodium chloride | 5.0 |
| Brom thymol blue | 0.08 |

| | |
|---|---|
| agar | 15.0 |
| distilled water | 1,000.0 |

| Medium 4 | |
|---|---|
| urea | 20.0 |
| dextrose | 1.0 |
| sodium chloride | 5.0 |
| peptone | 1.0 |
| monosodium phosphate | 2.0 |
| phenol red | 0.012 |

These components are dissolved in 100 ml. of distilled water and filtered through Seitz to achieve sterilization. To this medium is added a sterilized solution of 15 grams of Agar in 900 ml. of distilled water.

EXAMPLE 2

Identification Of Uropathogens

A plastic Petri dish with four compartments is charged with the four media of Example 1 in the separate compartments.

A second Petri dish with two compartments is charged with a blood brain heart agar medium in one compartment, and eosin methylene blue medium in the other.

Approximately 0.5 ml. of urine obtained under sterile conditions is spread on the surfaces of the media in the four compartment Petri dish. This group of cultures is for identification of uropathogens and for colony count.

With a 0.01 ml. platinum loop, the blood brain heart agar medium and eosin methylene blue medium are streaked with urine. In an emergency the urine is swabbed on the surface of 2 Mueller-Hinton Petri dishes and drug disks are placed on the surface of the medium.

After overnight incubation at 37°C. the color changes and the number of colonies and the drug susceptibility are recorded. If the urine has only one pathogen it is identifiable, but if the urine yields a mixed culture pure cultures must be obtained prior to identification. In case of doubt concerning the identification of a bacterial culture, routine sugars, lysine ornithine, malonate, gelatin and desoxyribonuclease media are inoculated. Enterobacteriaceae, Alcaligenes, Pseudomonas, Candida and enterococcus grow well on these media. Mimae-Herellae, Mycoplasma, diphtheroids, staphylococcus and streptococcus ($\alpha$, $\beta$ and $\gamma$) grow on brain heart blood agar.

The identification of Enterobacteriaceae is described in "Identification of Enterobacteriaceae" (3rd ed., Burgess Publishing Co., Minneapolis, 1972).

Drug susceptibility is routinely monitored by employing the Bauer-Kirby procedure reported in Bauer et al., Amer. J. Clin. Path., 45, 493(1966). The diameter of the zone of inhibition is measured in millimeters and compared with the Bauer-Kirby scale of resistance/susceptibility pattern.

EXAMPLE 3

Counting Of Bacteria Colonies

Media are cultured in the manner of Example 2, and the colonies are counted.

Sterile urine yields no colonies on our media and on the blood agar/eosin methylene blue medium. If there is a solid film of growth on our 4 media, the colony is more than 100,000 bacteria per ml. The following figures were obtained by comparing growth on 4 media in the Petri dish with dilution pour plate cultures of urine samples. Estimation of colony per ml. urine is as follows: no colonies on media equals sterile urine, 0 to 100 colonies equals less than 100 colonies per ml., more than 100 colonies equals 100 to 1,000 colonies per ml., countable colonies equals more than 10,000 colonies per ml. and uniform-heavy growth equals more than 100,000 colonies per ml.

Often Escherichia coli culture is immediately recognized by its metallic color and lack of urease and citrase activity. Klebsiella colonies are commonly mucoid--Proteus swarms. Pseudomonas produce at times bluish-green pigment and the colonies are ameboid or irregularly fimbriated.

The procedures described in the foregoing examples were tested with hundreds of urine samples and compared with prior art methods of uropathogen identification. Representative of literature describing prior methods are the following:

1. L. G. Smith et al., Ann. Intern. Med., 54, 66(1961).
2. J. D. Sleigh, Brit. Med. J., 1, 765(1965).
3. H. Seneca, J. Amer. Geriat. Soc., 13, 947(1965).
4. N. A. Hinton et al., Can. Med. Ass. J., 93 639(1965).
5. T. G. Sacks et al., J.A.M.A., 201, 1(1967).
6. A. I. Braude et al., J. Lab. Clin. Med., 57, 490(1961).
7. A. P. Shapiro et al., Ann. Intern. Med., 74, 861(1971)
8. K. A. Borchardt, Lab. Manag., 7, 47(1969).
9. A. L. Gandelman et al., Curr. Ther. Res., 7, 130(1965).
10. E. Grunberg et al., Appl. Microb., 18, 207(1969).
11. H. D. Isenberg et al., Appl. Microb., 22, 1126(1971).
12. P. B. Smith et al., Appl. Microb., 21, 1036(1971).
13. NASA Technical Brief 71-1-051(1971).

In one of its preferred embodiments the present invention provides a general procedure for rapid identification and evaluation of uropathogens which is readily amenable for practice in diagnostic laboratories, hospitals, clinics and physicians' offices. Such general procedure involves charging a four compartment Petri-type dish separately with (1) a medium for lactose and sucrose fermentation, (2) a medium for urea splitting, (3) a medium for citrate utilization and (4) a medium for hydrogen sulfide and indole production, and phenylalanine deamination; charging a two compartment Petri-type dish separately with (5) blood brain heart agar medium, and (6) eosin methylene blue medium; inoculating all of the media with test urine; culturing the media; identifying uropathogens; counting uropathogen colonies; and determining drug susceptibility of the uropathogens with Mueller-Hinton plates according to the Bauer-Kirby method. An elaboration of this general procedure is set forth in The Journal of Urology, 110, 446(1973).

What is claimed is:

1. As an article of manufacture, a diagnostic kit for the rapid identification of uropathogenic bacteria which comprises a Petri-type dish which is structurally divided and contains in separate compartments culture media consisting of medium (1) comprising peptone, saccharose, lactose, dipotassium phosphate, eosin, methylene blue, agar, distilled water; medium (2) comprising peptone, beef extract, peptonized iron, sodium thiosulfate, DL-phenylalanine, agar, distilled water; medium (3) comprising magnesium sulfate, ammonium dihydrogen phosphate, disodium phosphate, sodium citrate, sodium chloride, Brom thymol blue, agar, distilled water; and medium (4) comprising urea, dextrose, sodium chloride, peptone, monosodium phosphate, phenol red, agar and distilled water.

2. An article of manufacture in accordance with claim 1 wherein additional compartments are provided which contain culture media comprising (5) blood brain heart agar medium and (6) eosin methylene blue medium.

3. A procedure for rapid identification and evaluation and colony count of uropathogenic bacteria which comprises charging a four compartment Petri-type dish separately with medium (1) comprising peptone, saccharose, lactose, dipotassium phosphate, eosin, methylene blue, agar, distilled water; medium (2) comprising peptone, beef extract, peptonized iron, sodium thiosulfate, DL-phenylalanine, agar, distilled water; medium (3) comprising magnesium sulfate, ammonium dihydrogen phosphate, disodium phosphate, sodium citrate, sodium chloride, Brom thymol blue, agar, distilled water; and medium (4) comprising urea, dextrose, sodium chloride, peptone, monosodium phosphate, phenol red, agar and distilled water; charging a two compartment Petri dish separately with (5) blood brain heart agar medium, and (6) eosin methylene blue medium; inoculating all of the media with test urine; culturing the media; identifying uropathogens; counting uropathogen colonies; and determining drug susceptibility of the uropathogens with Mueller-Hinton plates according to the Bauer-Kirby method.

* * * * *